United States Patent [19]

Ford et al.

[11] Patent Number: 5,525,303

[45] Date of Patent: Jun. 11, 1996

[54] INTEGRAL FITTING AND FILTER OF AN ANALYTICAL CHEMICAL INSTRUMENT

[75] Inventors: Douglas W. Ford, West Linn, Oreg.; Kerry Nugent, Pleasanton, Calif.

[73] Assignee: Optimize Technologies, Inc., Oregon City, Oreg.

[21] Appl. No.: 416,481

[22] Filed: Apr. 4, 1995

Related U.S. Application Data

[63] Continuation of Ser. No. 106,393, Aug. 12, 1993, abandoned.

[51] Int. Cl.[6] .......................... B01D 15/08; B01L 11/00
[52] U.S. Cl. .................. 422/101; 422/69; 422/70; 422/81; 422/103; 210/198.2; 210/656; 73/61.52; 73/61.53
[58] Field of Search ................ 73/61.52, 61.53, 73/61.55, 61.56; 96/101, 106; 210/198.2, 656; 422/69, 70, 71, 101, 104, 103, 81

[56] References Cited

U.S. PATENT DOCUMENTS

| | | | |
|---|---|---|---|
| Re. 31,974 | 8/1985 | Brownlee | 210/198.2 |
| 3,855,130 | 12/1974 | Randau et al. | 210/198.2 |
| 3,878,099 | 4/1975 | Ogle | 210/198.2 |
| 4,026,803 | 5/1977 | Abrahams et al. | 210/198.2 |
| 4,084,718 | 4/1978 | Wadsworth | 215/247 |
| 4,093,550 | 6/1978 | Stahl et al. | 210/198.2 |
| 4,173,363 | 11/1979 | Stearns | 285/177 |
| 4,181,853 | 1/1980 | Abu-Shumays et al. | 250/304 |
| 4,187,177 | 2/1980 | Stahl | 210/198.2 |
| 4,228,007 | 10/1980 | Rausch et al. | 210/198.2 |
| 4,281,679 | 8/1981 | Stearns | 137/515.5 |
| 4,283,280 | 8/1981 | Brownlee | 210/198.2 |
| 4,451,363 | 5/1984 | Brownlee et al. | 210/198.2 |
| 4,457,846 | 7/1984 | Munk | 210/656 |
| 4,476,017 | 10/1984 | Scharff et al. | 210/94 |
| 4,512,899 | 4/1985 | Goodnight | 210/656 |
| 4,655,917 | 4/1987 | Shackelford et al. | 210/198.2 |
| 4,708,782 | 11/1987 | Andresen et al. | 204/299 R |
| 4,732,672 | 3/1988 | Kiang et al. | 210/198.2 |
| 4,737,284 | 4/1988 | Hauke et al. | 210/198.2 |
| 4,740,298 | 4/1988 | Andresen et al. | 210/198.3 |
| 4,765,890 | 8/1988 | Tehrani et al. | 210/198.2 |
| 4,792,396 | 12/1988 | Gundelfinger | 210/198.2 |
| 4,793,920 | 12/1988 | Cortes et al. | 210/198.2 |
| 4,882,047 | 11/1989 | Shalon | 210/198.2 |
| 4,882,063 | 11/1989 | Allington et al. | 210/659 |
| 4,888,112 | 12/1989 | Kronwald | 210/198.2 |
| 4,894,152 | 1/1990 | Colvin, Jr. et al. | 210/198.2 |
| 5,037,544 | 8/1991 | Snyder | 210/198.2 |
| 5,110,558 | 5/1992 | Romer | 422/101 |
| 5,169,522 | 12/1992 | Shalon et al. | 210/198.2 |
| 5,188,730 | 2/1993 | Kronwald | 210/198.2 |
| 5,194,225 | 3/1993 | Muller et al. | 422/70 |
| 5,227,059 | 7/1993 | Shepherd | 210/198.2 |
| 5,246,577 | 9/1993 | Fuchs et al. | 210/198.2 |

*Primary Examiner*—Jill Warden
*Assistant Examiner*—Harold Y. Pyon
*Attorney, Agent, or Firm*—Christensen, O'Connor, Johnson & Kindness

[57] ABSTRACT

An integral fitting and filter assembly (10) includes a tubular body (12) having a integral proximal fitting end (14) and an integral distal fitting end (16). A central passage (18) extends from the proximal fitting end to the distal fitting end of the body. A tubular sleeve (20) is slidably received within the central passage of the body. The tubular sleeve includes a stem portion (22) and a larger diameter head portion (24). The stem portion of the sleeve is packed with a selective chemical-absorbent packing material (26), that is retained within the sleeve by first and second porous plugs (28) secured within opposite ends of the stem portion of the sleeve. The sleeve is slidably inserted into the body, and is adjustably positioned longitudinally to provide a pre-column filter that may be used to mate with differently configured mating fittings, such as high-performance liquid chromatography instrument inlet fittings.

14 Claims, 3 Drawing Sheets

INTEGRAL FITTING AND FILTER OF AN ANALYTICAL CHEMICAL INSTRUMENT

This application is a continuation application based on prior application Ser. No. 08/106,393, filed on Aug. 12, 1993, now abandoned.

FIELD OF THE INVENTION

The present invention relates to analytical chemical instruments, and particularly to hardware for use with liquid chromatography instruments.

BACKGROUND OF THE INVENTION

Several types of chemical analytical equipment utilize columns that are packed with a selectively absorbent packing material. An analyte is introduced into one end of the column, and a carrier fluid is then run through the column. The length of time that the analyte is retained within the column can enable identification of the analyte. Such techniques are used in liquid chromatography, high performance liquid chromatography, and ion exchange apparatus, among others. For example, in high performance liquid chromatography (HPLC), a column that is packed with a silica gel, a polystyrene gel, or an ion exchange resin may be used. The analyte is introduced into one end of the column, and a carrier fluid consisting of a mixture of two liquid solvents is flushed through the column. The ratio of solvents making up the carder mixture is incrementally changed during the analysis.

Some chemical analytes may be irreversibly absorbed onto the packing material within an HPLC or other analytical column. As material is irreversibly absorbed by the packing material, the column eventually begins to provide inaccurate results. Such contamination necessitates periodic repacking of the column with fresh packing material, or replacement with a new column.

In order to prolong the life of a column, a pre-column filter is often used upstream of the inlet of the analytical column. The pre-column filter conventionally consists of a short length of stainless steel tubing that is packed with the same packing material as is used in the column. Each end of the tubing is provided with a nut and ferrule in order to enable the pre-column filter assembly to be connected between the solvent/analyte source and the analytical column inlet. The expense of producing such a pre-column filter is not inconsequential because of the fittings and assembly required. When the pre-column filter becomes contaminated through use, it must either be repacked or discarded. When discarded, the fittings on the pre-column filter assembly are typically wasted.

Several different manufacturers' HPLC instruments are commonly used in laboratories. Often different instrument manufacturers use different styles of column inlet fittings on their instruments. For example, various instruments may include column fittings produced by: Parker Hannifin Corporation, Cleveland, Ohio; Waters Division of Millipore, Milford, Mass.; or Valco Instruments Company Incorporated, Houston, Tex.

Each manufacturer's fittings have some conventional features in common, such as a 10–32 UNF internally threaded port. Each port also includes a beveled sealing surface. When a conventional pre-column filter is assembled to one of these fittings, a ferrule on the pre-column filter assembly seals against the inlet port sealing surface, and an externally threaded nut on the pre-column filter assembly engages with the internally threaded inlet port.

However, each component manufacturers' fittings are differently configured in other respects. For example, the longitudinal length of the beveled sealing surface of the inlet port fitting varies from manufacturer to manufacturer. Also, the length of pre-column filter tubing projecting beyond the ferrule on the pre-column filter that is accommodated within the inlet port varies from manufacturer to manufacturer. However, it is important to have the end of the pre-column filter tubing fully inserted into the inlet port of the instrument fitting regardless of the type of fitting utilized. This is to eliminate any significant dead volume within the mated fittings that would tend to slow the passage of analyte through the fitting assembly, resulting in attenuated retention time peaks. In order to accommodate different manufacturer's fittings, each pre-column filter assembly must often be differently constructed so that a corresponding length of tubing projects beyond the ferrule on the filter assembly.

SUMMARY OF THE INVENTION

The present invention provides an integral fitting and chemical filter, including a unitary body having a first integral fitting end and a second integral fitting end. The body defines a central passage extending from the first fitting end to the second fitting end. Selective chemical-absorbent packing material is retained within the central passage.

In a first preferred embodiment of the present invention, the integral fitting and chemical filter is an assembly comprising a body having a proximal fitting end and a distal fitting end, and defining a central passage extending from the proximal fitting end to the distal fitting end. The assembly also includes a tubular sleeve that is slidably received within the central passage of the body. A distal end of the sleeve is positionable to project an adjustable extent beyond the distal fitting end of the body. When the proximal and distal fitting ends of the body are connected to first and second mating fittings, such as fluid supply outlet and instrument inlet fittings, the distal end of the sleeve abuts a stop surface in the second mating fitting, and the first mating fitting contacts a proximal end of the sleeve. Filter media, such as selective chemical-absorbent packing material, is packed within the interior of the tubular sleeve, so that fluid passing between the first mating fitting and the second mating fitting flows through the filter media.

In a further aspect of the present invention, a method for filtering fluid that is being supplied from a fluid supply outlet to the inlet of an analytical instrument is provided. The method includes connecting a distal fitting end of the body of an integral fitting and filter assembly to the inlet of the analytical instrument. A filter member is then slidably positioned within a passage formed in the body, the passage extending from the distal fitting end to a proximal fitting end of the body, so that a distal end of the filter member seals against the inlet of the analytical instrument. The outlet of the fluid supply is connected to the proximal fitting end of the body so that the outlet of the fluid supply seals against a proximal end of the filter member. Fluid then is flowed from the fluid supply outlet, through the filter member, to the inlet of the analytical instrument.

In a second preferred embodiment of the present invention, the integral fitting and chemical filter is a one-piece unit, with the packing material being packed directly within the central passage of the body, and retained at each end by a porous plug. The second fitting end of the body is externally threaded, while the first fitting end is internally threaded. The integral fitting and chemical filter can thus be installed directly between the instrument inlet and a fluid supply outlet, with contaminants being irreversibly absorbed on the packing material within the integral fitting and chemical filter.

The present invention thus provides an integral fitting and filter that eliminates the need to install nuts and ferrules onto a tubing when producing a pre-column filter. Instead, the required fittings are formed directly on the unitary body of the integral fitting and filter. Because the integral fitting and filter is relatively inexpensive to produce, it can be discarded when the packing material is contaminated with an excessive amount of irreversibly absorbed material.

In the first preferred embodiment of the present invention utilizing an internal tubular sleeve packed with packing material within the body, the integral fitting and filter may be used on a variety of manufacturer's HPLC instrument fittings. Because the sleeve is slidably positioned longitudinally within the body, the length of the sleeve extending beyond the distal end of the body can be adjusted. This permits the sleeve to be fully inserted the length permitted by each mating fitting, so that dead volume is not created between the integral fitting and filter and the HPLC instrument inlet. The sleeve is simply inserted into the body as fully as permitted by the fitting of the HPLC instrument inlet, and then the fitting of the fluid supply outlet is threaded into the opposite end of the integral fitting and filter assembly sufficiently to compress the sleeve between the HPLC instrument inlet and the fluid supply outlet fittings. The sleeve is thus sealed on either end, while at the same time dead volume is avoided. The adjustable nature of this preferred embodiment of the present invention enables stocking of a single pre-column filter for use with a variety of manufacturers' HPLC instruments and associated hardware.

BRIEF DESCRIPTION OF THE DRAWINGS

The foregoing aspects and many of the attendant advantages of this invention will become more readily appreciated by reference to the following detailed description, when taken in conjunction with the accompanying drawings, wherein.

DETAILED DESCRIPTION OF THE PREFERRED EMBODIMENT

Figure 1:
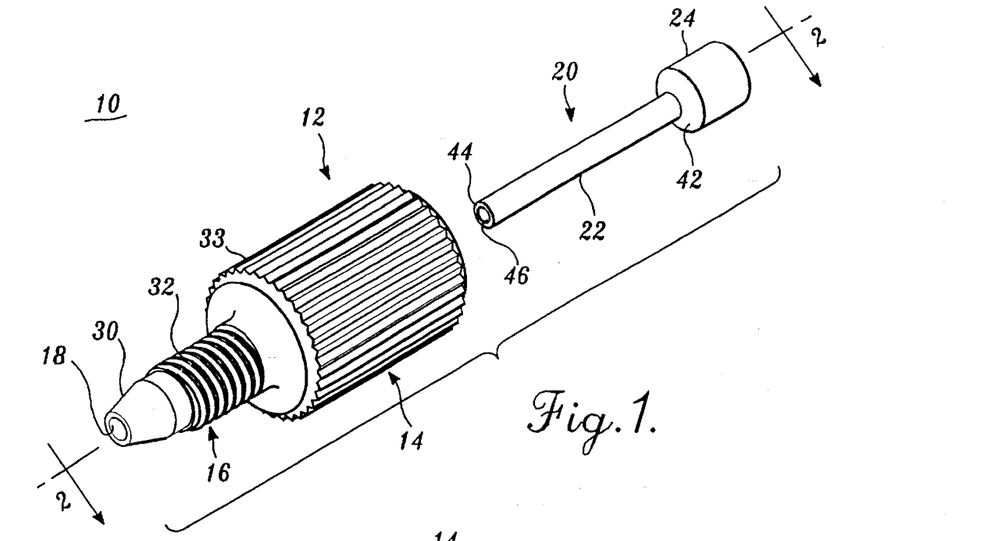
FIG. 1 is an exploded pictorial view of a two-piece fitting and filter assembly of the present invention.
Figure 2:
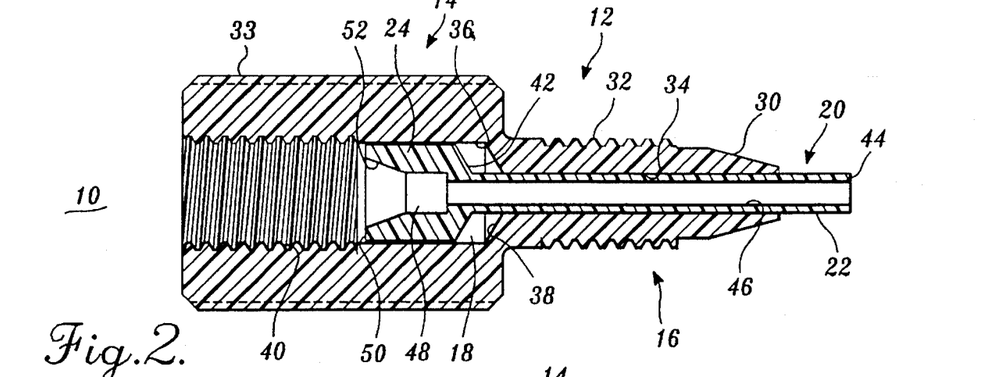
FIG. 2 is a cross-sectional view of the assembled two-piece fitting and filter assembly of FIG. 1, taken substantially along a plane indicated by line 2—2 in FIG. 1.
Figure 3:
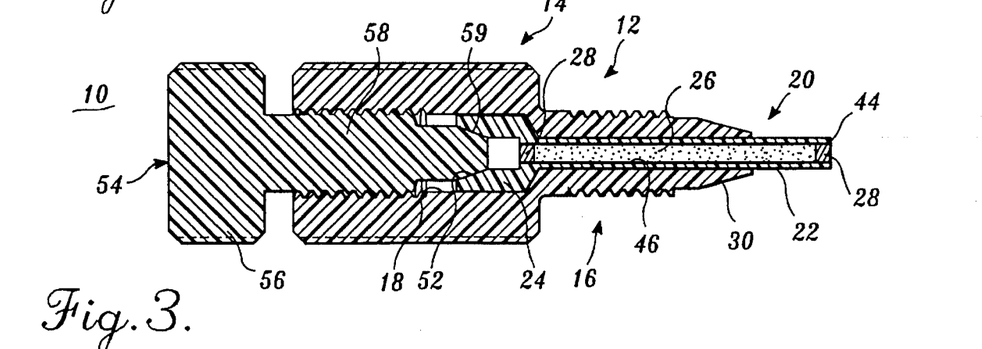
FIG. 3 is a cross-sectional view of the assembled fitting and filter assembly of FIG. 1, taken substantially along the same plane as in FIG. 2, including packing material within the tubular sleeve and a set plug installed in the body of the fitting and filter assembly.

A first preferred embodiment of an integral fitting and filter assembly 10 constructed in accordance with the present invention is shown in FIGS. 1–4C. The integral fitting and filter assembly 10 includes a tubular body 12 having a proximal fitting end 14 and a distal fitting end 16. A central passage 18 extends from the proximal fitting end 14 to the distal fitting end 16 of the body 12. A tubular sleeve 20 is slidably received within the central passage 18 of the body 12. The tubular sleeve 20 includes a stem portion 22 and a larger diameter head portion 24. As shown in FIGS. 2 and 3, the tubular sleeve 20 is inserted into the central passage 18 of the body 12, with the stem portion 22 of the sleeve 20 being received within the distal fitting end 16 of the body, and the head portion 24 of the sleeve 20 being received within the proximal fitting end 14 of the body 12. As shown in FIG. 3, the stem portion 22 of the sleeve 20 is packed with a selective chemical-absorbent packing material 26 that is retained by first and second porous plugs 28 secured within opposite ends of the stem portion 22 of the sleeve 20.

Referring to FIGS. 1 and 2, the body 12 is of unitary construction, and includes integral fittings formed on the proximal fitting end 14 and the distal fitting end 16. The proximal fitting end 14 thus defines the head of the body 12, and the distal fitting end 16 defines the shank of the body 12. Preferably, the body 12 is of one-piece construction, being molded, machined, or otherwise formed from a suitable material such as a thermoplastic resin or a metal. Most preferably, the body 12 is formed from a material that is solvent-resistant and biocompatible. One suitable material for use in making the body 12 is polyetheretherketone (PEEK).

The body 12 has an overall tubular configuration, with the diameter of the proximal fitting end 14 being greater than the diameter of the distal fitting end 16. The distal fitting end 16 has a tapered distal tip defining a frustoconical distal sealing surface 30. The distal fitting end 16 also has an externally threaded portion 32 formed between the distal sealing surface 30 and the proximal fitting end 14 of the body 12.

The proximal fitting end 14 has a knurled external surface 33 for ease of turning the body 12. Referring to FIG. 2, the central passage 18 has a small diameter filter portion 34 defined through the length of the distal fitting end 16 of the body 12. The filter portion 34 of the central passage 18 thus extends from the distal tip of the distal fitting end 16 to the juncture with the proximal fitting end 14 of the body. The central passage 18 then enlarges in diameter to form a fitting portion 36 of the central passage 18. The fitting portion 36 extends from the juncture with the filter portion 34 of the central passage 18 to the proximal tip of the proximal fitting end 14 of the body 12. At the juncture between the filter portion 34 and the fitting portion 36 of the central passage 18, the central passage 18 forms a beveled annular seat surface 38.

An internally threaded portion 40 of the fitting portion 36 of the central passage 18 extends from the proximal tip of the proximal fitting end 14 part way along the length of the fitting portion 36 of the passage. The internally threaded portion 40 and externally threaded portion 32 of the body 12 thus form integral fittings for connection of the fitting and filter assembly 10 between an analytical instrument and a fluid supply. In the preferred embodiment illustrated, both the externally threaded portion 32 and internally threaded portion 40 have ¼-10-32 UNF thread, as is commonly used for HPLC equipment. However, it should be apparent that other common threads, such as ¼-28, could be used.

The tubular sleeve 20 that is slidably received within the body 12 will now be described with reference to FIGS. 1–3. The sleeve 20 has a cylindrical head portion 24 that tapers on one face to define a seat surface 42. The degree of taper on the seat surface 42 corresponds to the degree of taper of the seat surface 38 within the central passage 18 of the body 12. The stem portion 22 of the tubular sleeve 20 extends longitudinally from the center of the seat surface 42. The stem portion 22 has a smaller diameter than the head portion 24, and is longer in length. The distal tip 44 of the stem portion 22 defines a flat annular stop surface.

Referring now to FIG. 2, the external diameter of the stem portion 22 corresponds to, and is slightly smaller than, the internal diameter of the filter portion 34 of the central passage 18. The external diameter of the head portion 24 corresponds to, and is slightly smaller than, the internal diameter of the fitting portion 36 of the central passage 18. The sleeve 20 is installed within the body 12 by orienting the stem portion 22 as the distal portion of the sleeve 20. The stem portion 22 is inserted into the fitting portion 36 of the central passage 18, and is then slidably inserted into the filter portion 34 of the central passage 18 of the body 12. The length of the stem portion 22 of the sleeve 20 is greater than the length of the filter portion 34 of the central passage, and thus the distal tip 44 of the stem portion 22 projects beyond the distal tip of the distal fitting end 16 of the body 12.

As shown in FIGS. 2 and 3, the tubular sleeve 20 can be adjustably positioned by sliding it within the body 12 to adjust the amount of the stem portion 22 of the sleeve 20 projecting beyond the end of the distal fitting end 16 of the body 12. When the sleeve 20 is fully inserted into the body 12, as shown in FIG. 3, the seat surface 42 of the sleeve 20 can sit against the seat surface 38 of the body 12.

The tubular sleeve 20 includes an internal passage 46. The internal passage 46 extends from the distal tip 44, through the stem portion 22, into the head portion 24. The internal passage 46 then enlarges in diameter to form a cylindrical chamber 48. Near a proximal tip 50 of the sleeve 20, the chamber 48 flares outwardly to form a beveled annular surface 52. The annular surface 52 thus defines a frustoconical recess formed centrally within the head portion 24 of the sleeve 20.

As shown in FIG. 3, the internal passage 46 of the sleeve 20 is filled with a filter media, preferably a selective chemical-absorbent packing material 26. The packing material 26 preferably is the same material that is used to pack the analytical column that will be downstream of the installed pre-column fitting and filter assembly 10. For example, a suitable packing material is a C-18 silica gel. Other conventional packing materials may be utilized, such as alumina, polystyrene gel, or ion-exchange resins.

The packing material 26 is retained in place by first and second porous plugs 28. Each porous plug 28 preferably is formed from a sintered metal flit, such as a sintered stainless steel frit. The cylindrical porous plugs 28 are preferably press-fit into the ends of the internal passage 46. Thus, a first porous plug 28 is positioned such that its face is even with the distal tip 44 of the stem portion 22. A second porous plug 28 is positioned spaced away from the first porous plug 28, at the juncture of the internal passage 46 and the cylindrical chamber 48 within the head portion 24 of the sleeve 20. The packing material 26 is packed tightly between the porous plugs 28.

Usage of the fitting and filter assembly 10 will now be described with reference to FIGS. 3 and 4A–4C. Prior to installation, a set plug 54 is threaded into the proximal fitting end 14 of the body 12. The set plug 54 has a knurled cylindrical head 56 and an externally threaded cylindrical shaft 58. The tip of the shaft 58 is beveled to define a set surface 59 corresponding to the annular surface 52 defined in the head portion 24 of the tubular sleeve 20. As the set plug 54 is threaded into the proximal fitting end 14 of the body, the distal tip of the shah 58 of the set plug 54 engages with the head portion 24 of the sleeve 20, pushing the tubular sleeve 20 forwardly in the direction of the distal fitting end 16 of the body 12. The set plug 54 is threaded inwardly to an extent such that the tubular sleeve 20 is positioned fully forwardly, as shown in FIG. 3. When so positioned, the distal tip 44 of the stem portion 22 of the sleeve 20 extends beyond the distal end of the body 12, and the seat surface 42 of the sleeve 20 contacts the seat surface 38 of the body 12. In the preferred embodiment illustrated, the distal tip 44 of the sleeve 20 projects a distance of approximately 0.2 cm beyond the distal tip of the body 12. In this manner, the tubular sleeve 20 is distally preset.

Figure 4A:
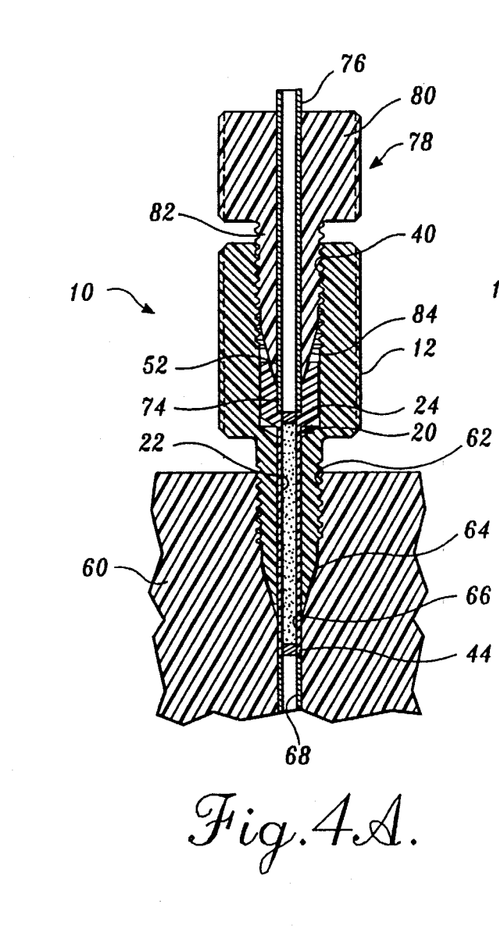
FIGS. 4A, 4B, and 4C are cross-sectional views, taken substantially along the same plane as in FIG. 2, of the packed two-piece fitting and filter assembly of FIG. 3 connected to three different styles of HPLC instrument inlet fittings, respectively, and mated in each instance with a fitting on the outlet end of a fluid supply tube.
Figure 4B:
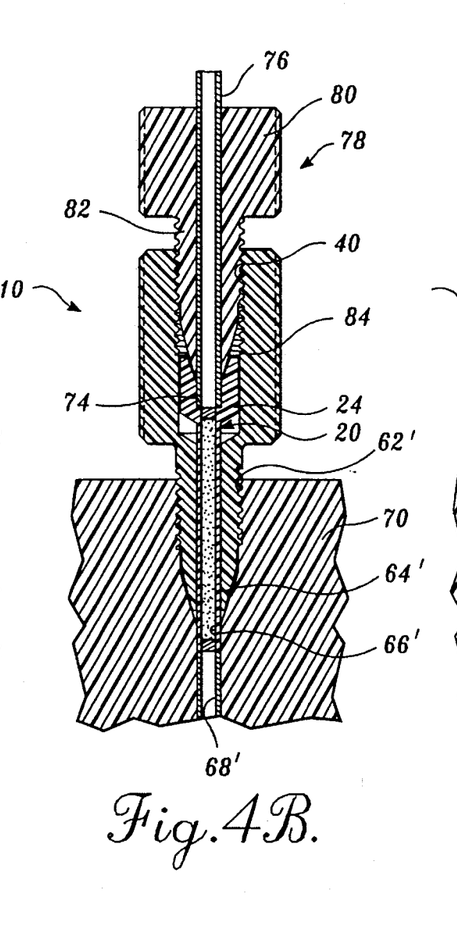
Figure 4C:
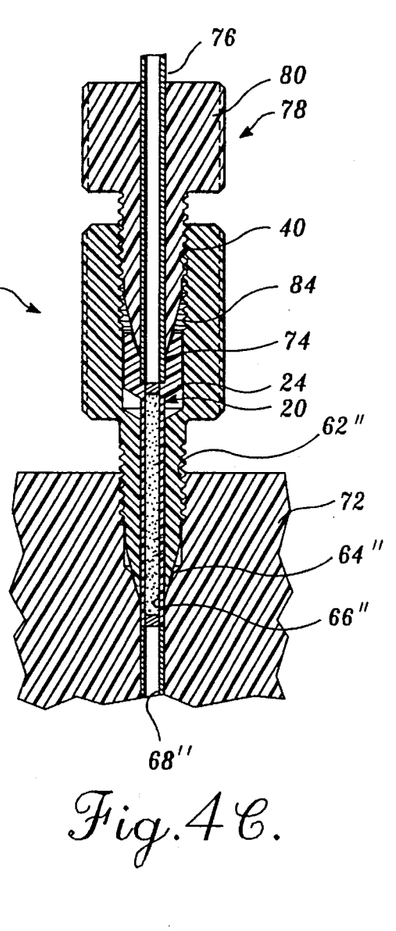

FIGS. 4A, 4B, and 4C show the fitting and filter assembly 10 installed in three different conventionally-styled HPLC fittings. FIG. 4A illustrates the fitting and filter assembly 10 connected to an HPLC inlet fitting 60 typical of that manufactured by Waters Division of Millipore Corporation, Milford, Mass. The fitting 60 has an internally threaded port 62 terminating in a beveled seat 64. The seat 64 opens into a cylindrical tube cavity 66. The tube cavity 66 terminates at the tip of an inlet tube 68.

FIG. 4B illustrates another conventional type of HPLC inlet fitting 70, such as is manufactured by Valco Instruments Company Incorporated, Houston, Tex., for example. Corresponding features of the fitting 70 are referred to with the same pan numbers as for the fitting 60, but with the addition of a prime ('). The internal configuration of the fitting 70 is substantially similar to those features of the fitting 60, except that the length of the tube cavity 66' in the fitting 70 is shorter than the length of the tube cavity 66 in the fitting 60. Both the beveled seat 64 in the fitting 60 and the beveled seat 64' in the fitting 70 define an angle relative to the longitudinal axis that is greater than the angle defined by the distal sealing surface 30 of the body 12 of the fitting and filter assembly 10.

FIG. 4C illustrates a third style of a fitting 72, such as is available from Parker Hannifin Corporation, Cleveland, Ohio. Corresponding features of the fitting 72 are identified with the same feature numbers as for fitting 60, but with the addition of a double prime ("). The fitting 72 of FIG. 4C is identically configured to the fitting 70 of FIG. 4B, except that the beveled seat 64" has a shorter longitudinal length, and the internally threaded port 62" is joined to the beveled seat 64" by an intermediate annular tapered surface.

To install the fitting and filter assembly 10, preset as shown in FIG. 3, in any of the instrument inlet fittings 60, 70, or 72, the preset plug 54 is first removed from the fitting and filter assembly. The body 12 is then threaded into the threaded port 62, 62', or 62". The threading of the body 12 continues until the distal tip 44 of the tubular sleeve 20 is fully inserted into the tube cavity 66, 66', or 66". As the body 12 is further threaded inwardly, the tubular sleeve 20 begins to slidably retract within the body 12. This continues until the distal sealing surface 30 of the body 12 contacts the corresponding beveled seat 64, 64', or 64" of the mating fitting. The distal sealing surface 30 of the body 12 seals against the mating instrument fitting 60, 70, or 72 in this manner, thereby serving as integral ferrule for the distal fitting end 16 of the body 12.

Because of the slidable disposition of the tubular sleeve 20 within the body 12, the sleeve 20 is able to project beyond the distal end of the body 12 an adjustable amount as required to completely fill the length of the tube cavity 66, 66', or 66" of the corresponding HPLC instrument fitting. The distal tip 44 of the stem portion 22 of the sleeve 20 abuts the tip of the inlet tube 68, 68', or 68" within the mating instrument fitting, and substantially no dead volume exists in each of these mated fittings. As shown by comparing FIG. 4A to FIGS. 4B and 4C, the amount of retraction of the tubular sleeve 20 within the body 12 depends on the dimensions of the mating instrument fitting 60, 70, or 72. In either case, the fitting and filter assembly 10 automatically adjusts to the correct length of sleeve 20 projecting beyond the body 12.

An outlet end 74 of a fluid supply tube 76 is then connected to the proximal fitting end 14 of the fitting and filter assembly 10, as shown in each of FIGS. 4A–4C. A nut 78 is carried axially on the outlet end 74 of the fluid supply tube 76. The nut 78 has a knurled head 80 and an externally threaded shaft 82 terminating in a beveled sealing surface 84. The outlet end 74 of the fluid supply tube 76 passes through the interior of the nut 78 and extends beyond the tip of the shaft 82.

To connect the fluid supply (not shown) to the fitting and filter assembly 10, the nut 78 is threaded into the internally threaded portion 40 of the body 12, until the tip of the outlet end 74 of the fluid supply tube 76 is received within the chamber 48 (FIG. 2) within the head portion 24 of the sleeve 20. The beveled sealing surface 84 of the nut 78 then contacts and seals against the annular surface 52 (FIG. 4A) formed within the head portion 24 of the sleeve 20.

In this fully coupled configuration (FIG. 4), the tubular sleeve 20 is longitudinally compressed between the nut 78 on the fluid supply tube 76 and the analytical instrument inlet fitting 60, 70, or 72. The filter formed by the packing material 26 (FIG. 3) inside the tubular sleeve 20 is thus sealed on each end to the fluid supply outlet tube 76 and analytical instrument inlet tube 68, 68', or 68". Liquid, such as a carrier solvent, can then flow from the fluid supply through the fluid supply tube 76, passing through the first porous plug 28 through the packing material 26 within the tubular sleeve 20, and exiting the second porous plug 28 into the analytical instrument supply inlet tube 68, 68', or 68".

Because the integral fitting and filter assembly 10 has few parts and is easily assembled, it is relatively inexpensive to manufacture. When the packing material 26 becomes contaminated, the entire fitting and filter assembly 10 can be replaced. Alternately, just the tubular sleeve 20 can be replaced.

Figure 5:
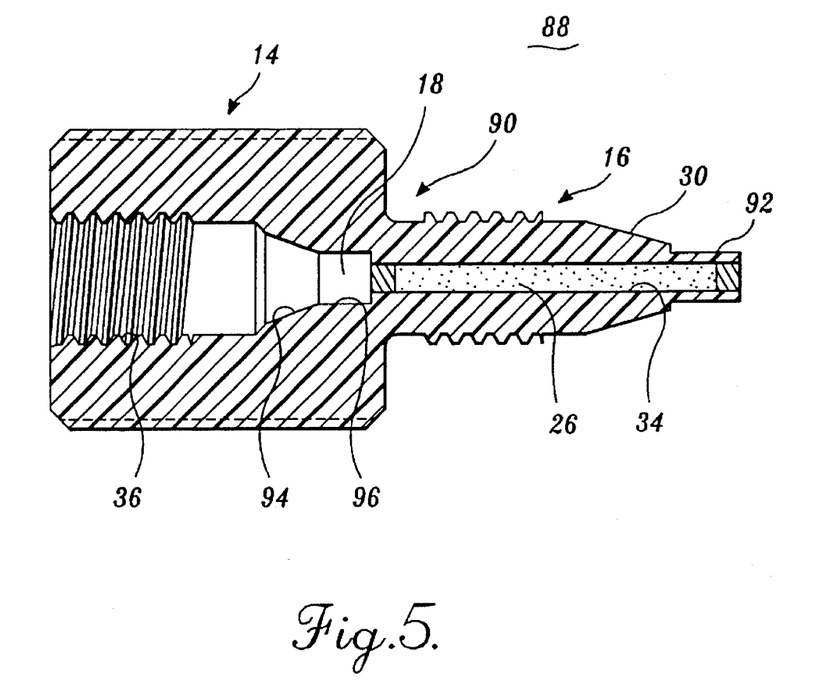
FIG. 5 illustrates a cross-sectional view of a one-piece integral fitting and filter assembly, with the cross section being taken through the longitudinal axis of the tubular body, and with the body being shown packed with filter packing material.

FIG. 5 illustrates an alternate one-piece integral fitting and filter assembly 88 constructed in accordance with the present invention. The integral fitting and filter assembly 88 includes a body 90 that is identically constructed to the previously described body 12, with the following exceptions. Those parts and features that are in common with the previously described integral fitting and filter assembly 10 are referred to using the same part numbers. No tubular sleeve 20 is provided within the integral fitting and filter assembly 88, so the body 90 is formed to incorporate these features in a non-adjustable fashion. The body 90 includes a proximal fitting end 14 and a distal fitting end 16. A tubular projection 92 is formed on the distal tip of the distal fitting end 16, extending beyond the distal sealing surface 30. The filter portion 34 of the central passage 18 extends through the tubular projection 92. This tubular projection 92 takes the place of the projecting distal tip of the tubular sleeve 20 in the fitting and filter assembly 10 previously described.

A beveled annular sealing surface 94 is formed by the central passage 18 within the body 90, between the filter portion 34 and the fitting portion 36 of the passage. A cylindrical chamber 96 is also formed by the central passage 18, between the sealing surface 94 and the filter portion 34 of the passage. The beveled surface 94 and the chamber 96 take the place of the annular surface 52 and chamber 48 (FIG. 2) of the tubular sleeve 20 in the integral fitting and filter assembly 10.

Packing material 26 fills the filter portion 34 of the central passage 18, and is retained by first and second porous plugs 28 that are press fit into each end of the filter portion 34 of the passage 18. The integral fitting and filter 88 is installed in the same manner as that previously described for the integral fitting and filter assembly 10, except that there is no slidable sleeve 20. Thus, the one-piece integral fitting and filter assembly 88 must be differently configured for each conventional type of corresponding mating instrument inlet fitting 60, 70, or 72.

Figure 6:
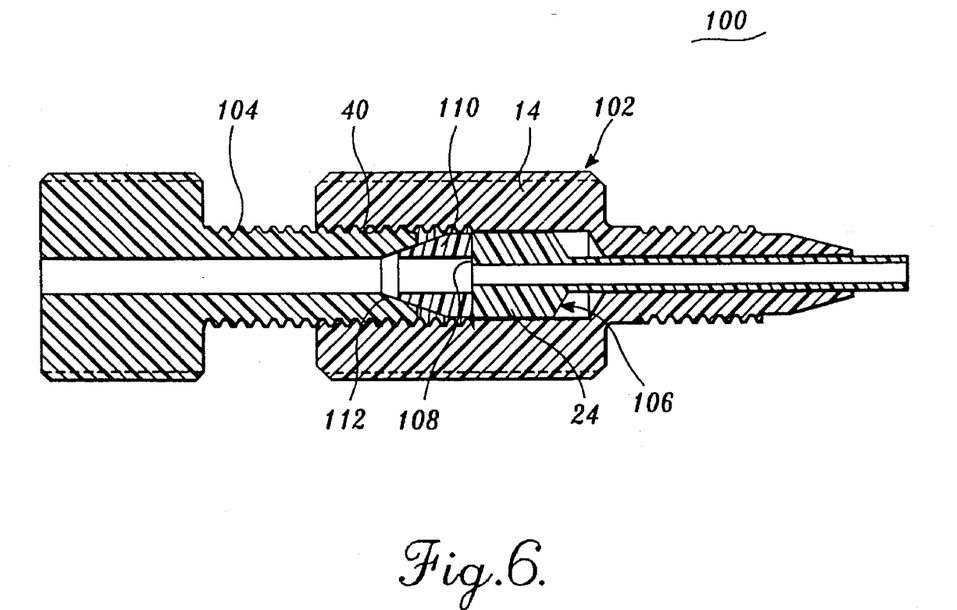
FIG. 6 illustrates a cross-sectional assembly view of an alternate version of a two-piece integral fitting and filter assembly, the cross section being taken through the longitudinal axis of the assembly, the assembly including a ferrule positioned adjacent the proximal end of the internal sleeve, which is illustrated without packing material, for mating with a ¼-28 UNF thread fluid supply fitting.

FIG. 6 illustrates a second alternate embodiment of the integral fitting and filter assembly 10 previously described. The integral fitting and filter assembly 100 illustrated in FIG. 6 is identically configured to the assembly 10 except as noted, thus corresponding pan numbers are used for those features and pans in common. The integral fitting and filter assembly 100 serves as an adapter between a second type of conventional fluid supply inlet fitting and the aforementioned instrument inlet fittings 60, 70, and 72. The fitting and filter assembly 100 includes a body 102 that is identically constructed to the previously-described body 12, except that the internally threaded portion 40 of the proximal fitting end 14 is threaded with a ¼-28 UNF internal thread. This enables the proximal fitting end 14 to receive a correspondingly externally threaded nut 104 on a fluid supply tube (not shown).

The fitting and filter assembly 100 also includes a tubular sleeve 106 that is identically configured to the previously-described tubular sleeve 20, except that the proximal end 108 of the head portion 24 is flat, rather than forming a beveled annular surface 52 as previously described. The flat side of a conventional frustoconical ferrule 110 is installed into the proximal fitting end 14 of the body 102, and sits against the distal end 108 of the sleeve 106. The tapered side of the ferrule 110 is received within and seals against a beveled recess 112 formed in the proximal end of the nut 104.

When the integral fitting and filter assembly 100 is installed within a selected HPLC inlet fitting, the tubular sleeve 106 is adjustably positioned as described previously. The tubular sleeve 106 is compressed between the HPLC instrument inlet 60, 70 or 72 and the ferrule 110 by tightening the nut 104.

While the foregoing fitting and filter assemblies 10 and 88 have been described for use with HPLC instruments, it can also be used with other analytical instruments, such as other liquid chromatography and gas chromatography instruments, and in other chemical analytical techniques. For example, fluid samples can be analyzed for presence of toxic materials or other contaminants through purge and trap techniques, whereby a sample of the fluid is injected through the filter medium of the fitting and filter assembly 10 or 88 on site for later laboratory analysis.

The integral fitting and filter assemblies 10, 88, and 100 above have been described with regard to certain conventional mating fittings, it should be readily apparent that the proximal fitting end 14 and distal fitting end 16 of each of these fitting and filter assemblies can be adapted to engage with alternate conventional fittings, by utilizing the proper thread and sealing surfaces, as will be readily appreciated by one of ordinary skill in the art based on the disclosure contained herein. While several preferred embodiments of the invention have been illustrated and described above, it will be appreciated that various other changes can be made therein without departing from the spirit and scope of the invention.

The embodiments of the invention in which an exclusive property or privilege is claimed are defined as follows:

1. An integral fitting and filter of an analytical chemical instrument comprising:

a one-piece body having a first integral fitting end and a second integral fitting end, and defining a central passage extending from the first fitting end to the second fitting end;

a tubular sleeve received within the central passage of the body and freely slidable along the length of the central passage for automatic longitudinal positioning of the sleeve during mating of the integral fitting and filter;

selective chemical-absorbent packing material packed within the interior of the tubular sleeve; and first and second porous plugs secured within each end of the tubular sleeve to retain the packing material within the interior of the tubular sleeve.

2. The integral and filter of claim 1, wherein:

the central passage of the body includes a fitting portion and a smaller diameter filter portion; and the sleeve includes a stem portion having an external diameter corresponding to the internal diameter of the filter portion of the body and insertable therein, and a head portion having an external diameter corresponding to the diameter of the fitting portion of the central passage.

3. The integral fitting and filter of claim 2, wherein the central passage further defines a tapered annular sealing surface between the fitting portion and the filter portion, and the exterior of the tubular sleeve defines a tapered external annular surface between the head portion and the stem portion that is capable of mating against the sealing surface in the central passage of the body.

4. The integral fitting and filter of claim 2, wherein the length of the stem portion of the sleeve is longer than the length of the filter portion of the central passage of the body, whereby when the tubular sleeve is fully inserted within the body, the end of the stem portion of the sleeve projects beyond the second integral fitting end of the body.

5. An integral fitting and filter assembly for connecting a first mating fitting in fluid flow communication with a second mating fitting, of an analytical chemical instrument comprising:

a one-piece body having a proximal fitting end and a distal fitting end, and defining a central passage extending from the proximal fitting end to the distal fitting end, the proximal and distal fitting ends of the body being connectable to first and second mating fittings, respectively;

tubular sleeve received within the central passage of the body and freely slidable along the length of the central passage for automatic longitudinal positioning of the sleeve during mating of the integral fitting and filter, with a distal end of the sleeve being positionable to project an adjustable extent beyond the distal fitting end of the body, such that when the proximal and distal fitting ends of the body are connected to the first and second mating fittings, respectively, the distal end of the sleeve abuts a stop surface in the second mating fitting and the first mating fitting contacts a proximal end of the sleeve, providing zero dead-volume connection of the sleeve to the first and second mating fittings; and filter media packed within the interior of the tubular sleeve, so that fluid passing between the first mating fitting and the second mating fitting flows through the filter media.

6. The integral fitting and filter assembly of claim 5, wherein the central passage includes an internally threaded fitting portion within the proximal fitting end of the body, and the distal fitting end of the body defines an externally threaded surface.

7. The integral fitting and filter assembly of claim 6, wherein the distal fitting end of the body further defines a tapered annular external sealing surface proximate the external threaded surface, and a beveled annular sealing recess is formed axially in the proximal end of the tubular sleeve.

8. The integral fitting and filter assembly of claim 5, wherein the proximal end of the tubular sleeve defines a proximal sealing surface.

9. The integral fitting and filter assembly of claim 8, wherein the proximal sealing surface is defined by a frustoconical recess formed axially into the proximal end of the sleeve, and the distal fitting end of the body defines an external frustoconical distal sealing surface.

10. The integral fitting and filter assembly of claim 5, wherein the filter media comprises a selective chemical-absorbent packing material, further comprising first and second porous plugs secured in spaced-apart relationship within the tubular sleeve to retain the packing material therein.

11. The integral fitting and filter assembly of claim 10, wherein the first and second porous plugs are secured within the proximal and distal ends of the sleeve, respectively.

12. The integral fitting and filter assembly of claim 5, wherein the central passage of the body includes a fitting portion and a smaller diameter filter portion, and the sleeve has a stem portion having an external diameter corresponding to the diameter of the filter portion of the central passage of the body, the stem portion of the sleeve being slidably received within the filter portion of the central passage, and a head portion having an external diameter corresponding to the diameter of the filter portion of the central passage and slidably received there within.

13. The integral fitting and filter assembly of claim 5, wherein the central passage of the body further defines a beveled annular seat between the fitting portion and the filter portion, and the sleeve defines a corresponding external frustoconical stop surface between the head portion and stem portion of the sleeve.

14. An integral fitting and filter assembly for installation between first and second mating connectors of an analytical chemical instrument comprising:

a one-piece body having first and second connector ends and defining a passage extending longitudinally from the first connector end to the second connector ends; and a filter member received within the passage of the body, and freely slidable along the length of the passage, such that when the first and second connector ends are connected to first and second mating connectors, respectively, the filter member is automatically adjustably positioned longitudinally within the body to seal in zero dead-volume connection against each of the first and second mating connectors so that fluid can flow between the first and second mating connectors, through the filter member.

* * * * *

UNITED STATES PATENT AND TRADEMARK OFFICE
CERTIFICATE OF CORRECTION

PATENT NO. : 5,525,303
DATED : June 11, 1996
INVENTOR(S) : D.W. Ford et al.

It is certified that error appears in the above-indentified patent and that said Letters Patent is hereby corrected as shown below:

| COLUMN | LINE | |
|---|---|---|
| 9 (Claim 2, | 38 line 1) | After "integral" insert --fitting-- |
| 9 (Claim 5, | 63 line 3) | Delete "," after --fitting-- and reinsert it after --instrument-- |
| 10 (Claim 5, | 4 line 11) | Before "tubular" insert --a-- |
| 10 (Claim 14, | 67 line 3) | After "instrument" insert --,-- |

Signed and Sealed this

Third Day of December, 1996

Attest:

BRUCE LEHMAN

Attesting Officer        Commissioner of Patents and Trademarks